April 20, 1954 H. I. BURKEY Plant Pat. 1,270
SNAPDRAGON PLANT
Filed May 22, 1953
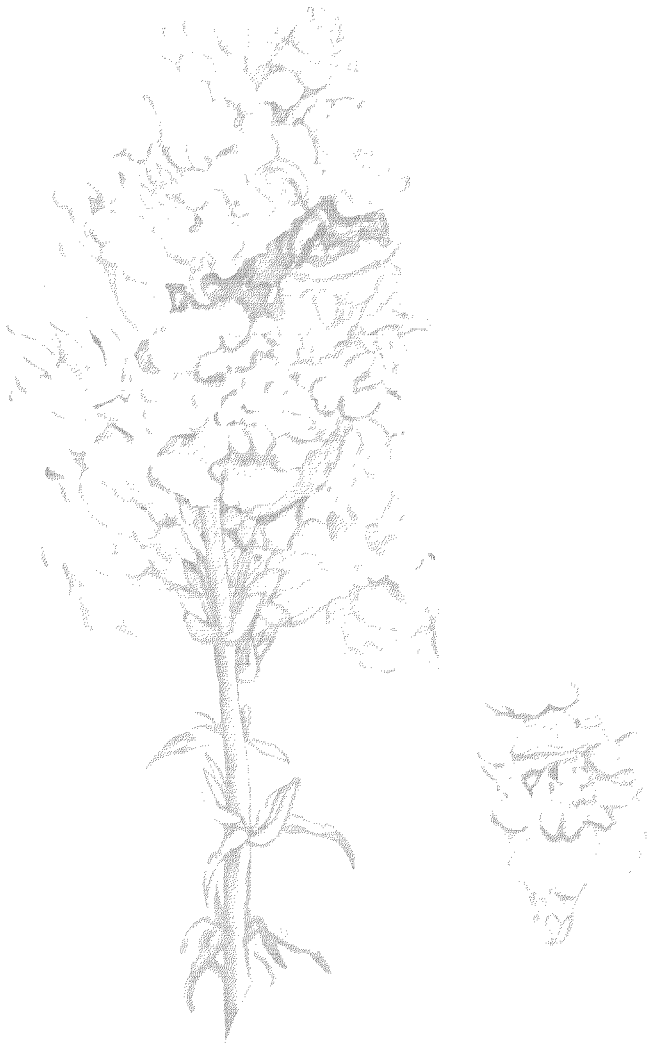
INVENTOR
HAROLD IVAN BURKEY
BY Toulmin & Toulmin
ATTORNEYS Patented Apr. 20, 1954

Plant Pat. 1,270

UNITED STATES PATENT OFFICE 1,270

SNAPDRAGON PLANT

Harold Ivan Burkey, Stuart, Fla.

Application May 22, 1953, Serial No. 356,922

1 Claim. (Cl. 47—60)

My present discovery relates to a new and distinct variety of snapdragon (Antirrhinum) plant which originated as a seedling resulting from a cross of unnamed seedling parents.

This new variety has been asexually reproduced by cuttings in my greenhouses at Mount Vernon, Ohio, and farm in Stuart, Florida, and has remained true to type and the herein described characteristics through the propagation of over 3,000 plants during a period of two years. There are presently 3,000 plants in existence at my farm in Stuart, Florida. No seeds have been produced by this new variety so all propagation must be asexual.

This new variety of snapdragon shows a pronounced reduplication of its petal-like parts and is sharply distinguished from other double snapdragon by the profusion of blossoms of a pleasing, distinctive, deep pink coloration; the absence of excessive lateral shoots; the variety is vigorous and easy to propagate, has a hard stiff stem and exhibits a fragrance. The variety is further characterized by its ability to bloom in the winter months in greenhouses in the Great Lakes region.

The accompanying illustrations show in full color a view embodying the invention and a view embodying the invention and a smaller front view of the flower of the new variety.

Referring to the illustrations the upper petal lobes, which are integral with the corolla tube, are oppositely disposed, two in number, curl backwardly, are of substantially equal size and have their center edges overlapping; the lower petal lobes are three in number, curl backwardly to partially cover the corolla tube, are crinkled on the edges and overlap each other slightly.

True functional stamens are not present but the usual six to eight stamens bear at their upper ends small pink wrinkled petals; approximately one-half of these stamens, usually those on the lower lobes, have yellow markings which extend up to the pink of the small petals and set off the distinctive pink coloration of the petals.

The plant has a hard, stiff stem, and the length of the stem and of the spike vary with conditions such as the time of year, weather and age; at maturity the stem may have a considerable height, a length of six feet not being unusual around the stem; the flowers are closely grouped and present a compact appearance.

The upper end of the spike has a plurality of flower buds with accompanying bracts and these progressively open as the variety ages. In the embodiment of the invention illustrated the spikes are somewhat short as the illustration was made at a time somewhat before full growth had been attained.

As shown in the drawings and particularly in the smaller figure the corolla tube which carries the petal lobes has in the lower portion a slightly lavender tint, which tint is emphasized if, as occasionally happens, a number of the corolla tubes are in close, visible proximity. The bluish blue-red or lavender of the corolla tube emerges into the distinctive and characteristic deep pink of the petals. The petals themselves are slightly darker at the edges than in the body and give to the variety the distinctive pink coloration; the yellow non-functional stamens protrude centrally of the flower and enhance the overall appearance.

The color designations of the variety according to "A Dictionary of Color" by Maerz and Paul are as follows:

| | Plate | Letter | Number |
|---|---|---|---|
| Main flower color-lobes | 49 | J | 4 |
| Edge coloration-lobes | 49 | J | 6 |
| Petals or stamens | 49 | J | 5 |
| Stamen markings | 9 | C | 4 |
| Corolla tube | 43 | I | 5 |
| Stem | 21 | G | 7 |
| Sepals | 20 | F | 6 |
| Leaves | 21 | F | 8 |

Having thus disclosed my discovery I claim:

A new and distinct variety of double snapdragon plant characterized particularly by its pleasing, distinctive characteristic deep pink coloration of the flowers; the compactness of the flowers; the absence of excessive lateral shoots; its vigor and hard stiff stems; and its ability to bloom in the winter months in greenhouses in the Great Lakes region.